United States Patent [19]
Jackson

[11] Patent Number: 5,472,582
[45] Date of Patent: Dec. 5, 1995

[54] ANALYSIS OF CARBOHYDRATES USING 2-AMINOACRIDONE

[75] Inventor: Peter Jackson, Fulbourn, United Kingdom

[73] Assignee: Astromed Limited, Cambridge, United Kingdom

[21] Appl. No.: 89,694

[22] Filed: Jul. 9, 1993

Related U.S. Application Data

[63] Continuation-in-part of Ser. No. 52,785, Apr. 23, 1993, which is a continuation-in-part of Ser. No. 686,584, May 7, 1991, Pat. No. 5,113,642.

[51] Int. Cl.$^6$ .................... G01N 27/26; G01N 27/447
[52] U.S. Cl. .................... 204/180.1; 204/182.8; 204/299 R; 536/18.7; 536/55
[58] Field of Search .................... 204/180.1, 182.8, 204/182.9, 299 R; 536/18.7, 55, 55.1, 31, 45

[56] References Cited

U.S. PATENT DOCUMENTS

| | | | |
|---|---|---|---|
| 4,462,993 | 7/1984 | Kovács et al. | 536/55 X |
| 4,852,137 | 7/1989 | Mackay | 378/62 |
| 4,874,492 | 10/1989 | Mackay | 204/182.8 |
| 4,975,165 | 12/1990 | Brandley | 204/182.1 |
| 5,019,231 | 5/1991 | Brandley et al. | 204/182.1 |
| 5,035,786 | 7/1991 | Brandley et al. | 204/182.1 |
| 5,104,508 | 4/1992 | Williams et al. | 204/182.8 |

FOREIGN PATENT DOCUMENTS

WO92/11531  7/1992  WIPO.

OTHER PUBLICATIONS

Jackson, "Polyacrylamide gel electrophoresis of reducing saccharides labeled with the fluorophore 2-aminoacridone: Subpicomolar detetction using an imaging system based on a cooled charge-coupled device," *Anal. Biochem.* 196:238–244 (1991).

Ernst Koller et al. "Fluorometric Continuous Kinetic Assay of α-Chymotrypsin Using New Protease Substrates Possessing Long-Wave Excitation and Emission Maxima" *Analytical Biochemistry*, 171, (1988) 393–397.

Martinez, J., et al., "The Role of Sialic Acid in the Dysfibrinogenemia Associated With Liver Disease: Distribution of Sialic Acid on the Constituent Chains," *Blood*, 61:1196–202 (1983).

Parekh, R. B., et al., "Association of rheumatoid arthritis and primary osteoarthritis with changes in the glycosylation pattern of total serum IgG," *Nature*, 316:452–457 (1985).

Winter, G. and Milstein, C., "Man-made antibodies," *Nature* 349:293–299 (1991).

Lorincz, A. E., et al., "The Early Laboratory Diagnosis of Mucopolysaccharidoses," *Ann. Clin. Lab. Sci.* 12:258–266 (1982).

Rademacher, T. W., et al., "Glycobiology," *Ann. Rev. Biochem.* 57:785–838.

(List continued on next page.)

*Primary Examiner*—John Niebling
*Assistant Examiner*—John S. Starsiak, Jr.
*Attorney, Agent, or Firm*—Albert P. Halluin; Pennie & Edmonds

[57] ABSTRACT

The present invention provides for the use of the fluorescent label 2-aminoacridone for use in separating carbohydrate mixtures and analyzing the structure of carbohydrates. Carbohydrates for analysis may be labeled by 2-aminoacridone and subsequently separated from one another by electrophoresis. The electrophoresis may be in one or two dimensions. Band produced by the electrophoresis may be visualized and quantitated directly by UV illumination or by means of a charge coupled device for photoelectric detection. 2-aminoacridone labelling of carbohydrate may also be used to analyze the structure of carbohydrates by cleaving (or adding to) various 2-aminoacridone labeled carbohydrates by carbohydrate modifying enzymes of known specificity, and subsequently separating the carbohydrates by electrophoresis in either one or two dimensions. The subject invention also provides for kits for performing 2-aminoacridone labelling and electrophoresis.

20 Claims, 10 Drawing Sheets

OTHER PUBLICATIONS

Sewell, A. C., et al., "Comprehensive Urinary Screening for Inborn Errors of Complex Carbohydrate Metabolism," *Klin Wochenschr*, 57:581–585 (1979).

Jackson, P., "The use of polyacrylamide-gel electrophoresis for the high-resolution separation of reducing saccharides labelled with the fluorophore 8-aminoaphthalene-1, 3,6-trisulphonic acid," Biochem. J. 270:705–713 (1990).

ANALYSIS OF CARBOHYDRATES USING 2-AMINOACRIDONE

CROSS REFERENCE TO RELATED APPLICATION

This reference is a continuation-in-part of application Ser. No. 08/052,785, filed Apr. 23, 1993, which is a continuation-in-part of application Ser. No. 07/686,584, now U.S. Pat. No. 5,113,642 filed May 7, 1991, both of which are incorporated herein by reference.

FIELD OF THE INVENTION

This invention relates to the analysis of carbohydrate structure and the separation and quantitation of mixtures of carbohydrates present in a sample.

BACKGROUND

Carbohydrate moieties of glycoconjugates are involved in numerous important biological processes. Sharon, N. (1984) Trends Biochem. 9, 198–202; Feizi, T. & Childs, R. A. (1985) Trends Biochem. Sci. 10, 24– 29; Feizi, T. Childs, R. A. 91987) Biochem. J. 245, 1– 11. In addition to their metabolic and storage roles, carbohydrates are covalently attached to numerous other molecules such as proteins and lipids. Molecules such as glycoproteins and glycolipids are generally referred to as glycoconjugates. The biological importance of the carbohydrate portion of glycoconjugates can be seen, for example, in the role they play in affecting the ability of glycoproteins to perform their biological functions, including such functions as ligand or receptor recognition.

As a consequence of their diverse and important biological functions, aberrations in the synthesis, degradation, or modification of carbohydrates may give rise to several diseases. Similarly many diseases may alter the body's physiology so as to give rise to altered carbohydrate metabolism or the improper glycosylation of proteins, lipids and other glycoconjugates in the body.

Many of the biologically active carbohydrates in the body are polysaccharides and oligosaccharides that are produced in a variety of related forms rather than having a single defined structure. These families of related carbohydrates are frequently found to be components of the same glycoprotein. These families of glycoproteins that share the same polypeptide structure, but display variation in the glycosylation pattern have been referred to as glycoforms, Rademacher, et al, *Ann. Rev. Biochem.*, 57:789–838 (1988).

The relative abundance of members of glycoform family members has been shown to vary in accordance with certain disease states. For example, the disfibrinogenemia associated with liver disease has been associated with variations in the glycosylation of fibrinogens, Martinez, J., et al, *Blood*, 61:1196– 202 (1983), and rheumatoid arthritis has been associated with changes in glycosylation of IgG, Parekh et al, *Nature*, 316:452–457 (1985).

Diseases based on improper metabolism of carbohydrates from glycoconjugates are well known. The general category of diseases is known by a variety of names, including lysosomal storage disorders, heteroglycanoses, inborn errors of complex carbohydrate metabolism, mucopolysaccharidoses and others. Each of these diseases is the result of a genetic inability to produce one or more of the enzymes required for the stepwise degradation of glycoproteins, mucopolysaccharides or glycolipids, or the carbohydrate portion of said glycoconjugates.

When one of these enzymes in the degradation pathway is incorrectly produced or missing completely, the molecule produced in the last working step of the degradation pathway accumulates due to the body's inability to further cleave the molecule. Over time, the compound that cannot be degraded accumulates to such an extent that it impedes normal biological function in a wide variety of cells throughout the body.

The consequences of this type of genetic defect vary among the different enzyme deficiencies, but the symptoms of these diseases may include organomegaly, corneal opacities, skeletal abnormalities and progressive mental retardation.

Thus, it is of interest to provide a general technique for the diagnosis of a variety of diseases characterized by altered levels of carbohydrates in which the diagnostic technique does not require an a priori detailed knowledge of the structure of the carbohydrates.

In order to accomplish this objective, it is necessary to develop a means for detecting carbohydrates, quantitating them and determining their chemical structures. Attempts to elucidate carbohydrate structure have depended on purification techniques such as high performance liquid chromatography (h.p.l.c.) and other chromatographic methods. Subsequent structural analysis has been performed by a combination of classical derivatization and degradation procedures, mass spectrometry (m.s.) and nuclear magnetic resonance (n.m.r.). McNeil, M., Darvill, A. G., Aman, P., Franzen, L. E. & Albersheim, P. (1982) Methods Enzymol. 83, 3–45; Barker, R., Nunez, H. A., Roseyear, P. & Serianni, A. S. (1982) Methods Enzymol. 83, 58– 69; White, C. A. & Kennedy, J. F. (1986) in Carbohydrate Analysis, A Practical Approach (Chaplin, M. F. & Kennedy, J. F., eds.). pp. 37–54, IRL Press, Oxford; Welply, J. K. (1989) Trends Biotechnol. 7, 5– 10. Although these are powerful methods, they have significant limitations. The quantities of material required for some analyses can be relatively large compared with that which is available from many specific biological sources. In addition, the equipment required for these methods is expensive and requires considerable expertise and technical support, which tends to restrict their use to few laboratories.

In order to overcome some of these disadvantages, several workers have used specific glycosidases to degrade complex oligosaccharides and have deduced their structures after separating the degradation products by various chromatographic and electrophoretic techniques. Wang, W. T., LeDonne, Jr., N. C., Ackerman, B. & Sweeley, C. C. (1984) Anal. Biochem. 141, 366–381; Welply, J. K. (1989) Trends Biotechnol. 2, 5–10; Tomiya, N. Kurono, M., Ishihara, H. Tejima, S., Endo, S., Arata, Y. & Takahashi, N. (1987) Anal. Biochem. 163, 489–499; Wenn, R. V. (1975) Biochem. J. 145, 281–285; Montreuil, J. Bougqulet, S., Debray, J. Pournet, B., Spik, G. & Strecker, G. (1986) in Carbohydrate Analysis: A Practical Approach (Chaplin, M. F. & Kennedy J. F., eds.), pp. 143–204, IRL Press, Oxford; Kobata, A. (1979) Anal. Biochem. 100, 1–14; Tarentino, A. L. Trimble, R. B. & Plummer, Jr., T. H. (1989) Methods Cells Biol. 32, 11–139. This type of analysis can be used with picomolar quantities of material. In order to enable the sensitive detection of such quantities, a number of methods have been described in which saccharides and glycopeptides have been labelled with either $^3H$, chromophores or fluorophores and the derivatives separated either chromatographically or electophoretically. Weitzman, S. Scott, V. & Keegstra, K. (1979) Anal. Biochem. 97, 438–449; Wang, W. T., LeDonne, Jr., N.

C., Ackerman, B. & Sweeley, C. C. (1984) Anal. Biochem. 141, 366–381; Hase, S., Ikenaka, T. a Matsushima, Y. (1979) J. Biochem. (Tokyo) 85, 989–994; Prakash, C. & Vijay, I. A. (1983) Anal. Biochem. 128, 41–46; Tomiya, N. Kurono, M., Ishihara, H. Tejima, S., Endo, S., Arata, Y. & Takahashi, N. (1987) Anal. Biochem. 163, 489–499; Wenn, R. V. (1975) Biochem. J. 145, 281–285; Narasimhan, S., Harpaz, N., Longmore, G. Carver, J. P., Grey, A. A. & Schachter, H. (1980) J. Biol. Chem. 225, 4876–4884; Hase, S., Ibuki, T. & Ikenaka, T. (1984) J. Biochem. (Tokyo) 95, 197–203; Poretz, R. D. & Pieczenik, G. (1981) Anal. Biochem. 115, 170– 176; Das, O. P. & Henderson, E. J. (1986) Anal. Biochem. 158, 390–398; Towbin, H., Schoenenberger, C. A., Braun, D. G. & Rosenfelder, G. (1988) Anal. Blochem. 173.1–9; Maness, N. O. & Mort, A. J. (1989) Anal. Biochem. 178, 248–254; Hara, S., Yamaguchi, M. Takemori, Y., Furuhata, K., Ogura, H. & Nakamura, M. (1989) Anal. Biochem. 179, 162–166; Honda, S., Iwase, S., Makino, A. & Fujiware, S. (1989) Anal. Biochem. 176, 72–77.

Similarly, the diagnosis of carbohydrate metabolism disorders has historically been difficult because few methods exist for the separation, detection and identification of a wide variety of complex carbohydrates. The two main methods that have been employed are carbohydrate staining techniques and chromatographic separation and detection methods.

The carbohydrate staining techniques, including the Berry Spot Test and the dimethylmethylene blue (DMB) assay rely on a specific reaction between a chemical dye and a specific class of oligosaccharides. The major application of these methods have been with the mucopolysaccharidoses, which are disorders of glycosaminoglycan degradation. These tests have been proposed for large scale screening, but they are limited to the specific disorders for which the chemistry is designed, and the tests have had a problem with a large number of false positive diagnoses. Sewell, et al, *Klin Wochenschr,* 57:581–585 (1979), or Lurincz, et al, *Ann. Clin. Lab. Sci.,* 12:258–266 (1982).

Chromatographic separation of oligosaccharides from glycoconjugates has also been proposed as a screening technique for these diseases, but there is not one chromatographic technique or set of chromatographic conditions that will facilitate the separation of the range of carbohydrate-based compounds that accumulate in all of these diseases. Thin layer chromatography (TLC), high performance liquid chromatography and gas chromatography have some utility in the diagnosis of the carbohydrate metabolic diseases, but they have found limited acceptance in clinical laboratories as a result of their limitations and/or complexity.

A new type of procedure has been described in which reducing saccharides are derivatized with fluorophores and the derivatives separated by one-dimensional polyacrylamide gel electrophoresis (PAGE). The fluorophore assisted carbohydrate electrophoresis technique is described in detail in U.S. Pat. Nos. 4,874,492 and 5,104,508, which are herein incorporated by reference. Fluorophore assisted carbohydrate electrophoresis permits the electrophoretic separation of a complex mixture of carbohydrates into distinct bands on a gel. Prior to electrophoresis, a carbohydrate mixture for analysis is treated with a fluorophore label that combines with the reducing end of the carbohydrates for analysis. The fluorophore label permits the quantitative measurement of the labeled carbohydrates by fluorescence. The fluorophore label either is charged or coupled with a charge imparting species when the fluorophore itself is uncharged. Thus the label not only fluorescently tags the carbohydrates, but imparts an ionic charge, permitting hitherto uncharged carbohydrates to migrate in an electric field.

After the carbohydrates have been labeled, the sample is subsequently subjected to polyacrylamide gel electrophoresis, or similar electrophoresis separation means, in order to separate and concentrate the labeled carbohydrates into bands. The separated carbohydrates may be visualized directly by photoelectric menus fluorescence under U.V. light and the banding patterns stored photographically. Alternatively the separated carbohydrates may be visualized by photoelectric means, including laser-scanner photomultiplier tube systems and cooled charge coupled devices (CCD). CCD's are semiconductor imaging devices that permit the sensitive detection of emitted light. CCDs and their uses are described in U.S. Pat. Nos. 4,874,492 and 4,852,137 which are herein incorporated by reference. The image produced by the CCD may be subsequently transferred to a computer wherein the bands may be analyzed with respect to intensity, mobility, standards, and the like.

When performing fluorophore assisted carbohydrate electrophoresis diagnosis, electrophoretic separation should take place to an extent sufficient to independently resolve bands of diagnostic carbohydrates specific for the disease of interest. Electrophoresis may proceed past the point where some carbohydrates have been removed from the electrophoresis separation medium.

Suitable fluorescent labels for use in fluorophore assisted carbohydrate electrophoresis include 8-aminonapthalene-1, 3,6-trisulphonic acid (ANTS), 1-amino-4-napthalene sulfonic acid (ANSA), 1-amino- 6,8-disulphonic acid (ANDA), lucifer yellow and 2-aminoacridone. The present invention is particularly directed toward fluorophore assisted carbohydrate electrophoresis wherein 2-aminoacridone is employed as the fluorescent labelling reagent.

SUMMARY OF THE INVENTION

According to the present invention there are provided methods of separating, distinguishing and quantitating carbohydrate substances or mixtures of carbohydrate substances, comprising labelling carbohydrate substances with 2-aminoacridone, applying the labelled substances to an electrophoretic gel, running the gel in either one or two dimensions to cause differential migration of different labelled substances, and quantitating the carbohydrate substances after detection by UV illumination or with a charge coupled device. The subject invention also provides for carbohydrate substances labeled by 2-aminoacridone. Another aspect of the invention are various kits for labeling carbohydrate substances with 2-aminoacridone or separating carbohydrates labeled by 2-aminoacridone.

DESCRIPTION OF THE FIGURES

The invention will be further described, by way of illustration, in the following Example and by reference to the accompanying drawings, in which.

Figure 1:
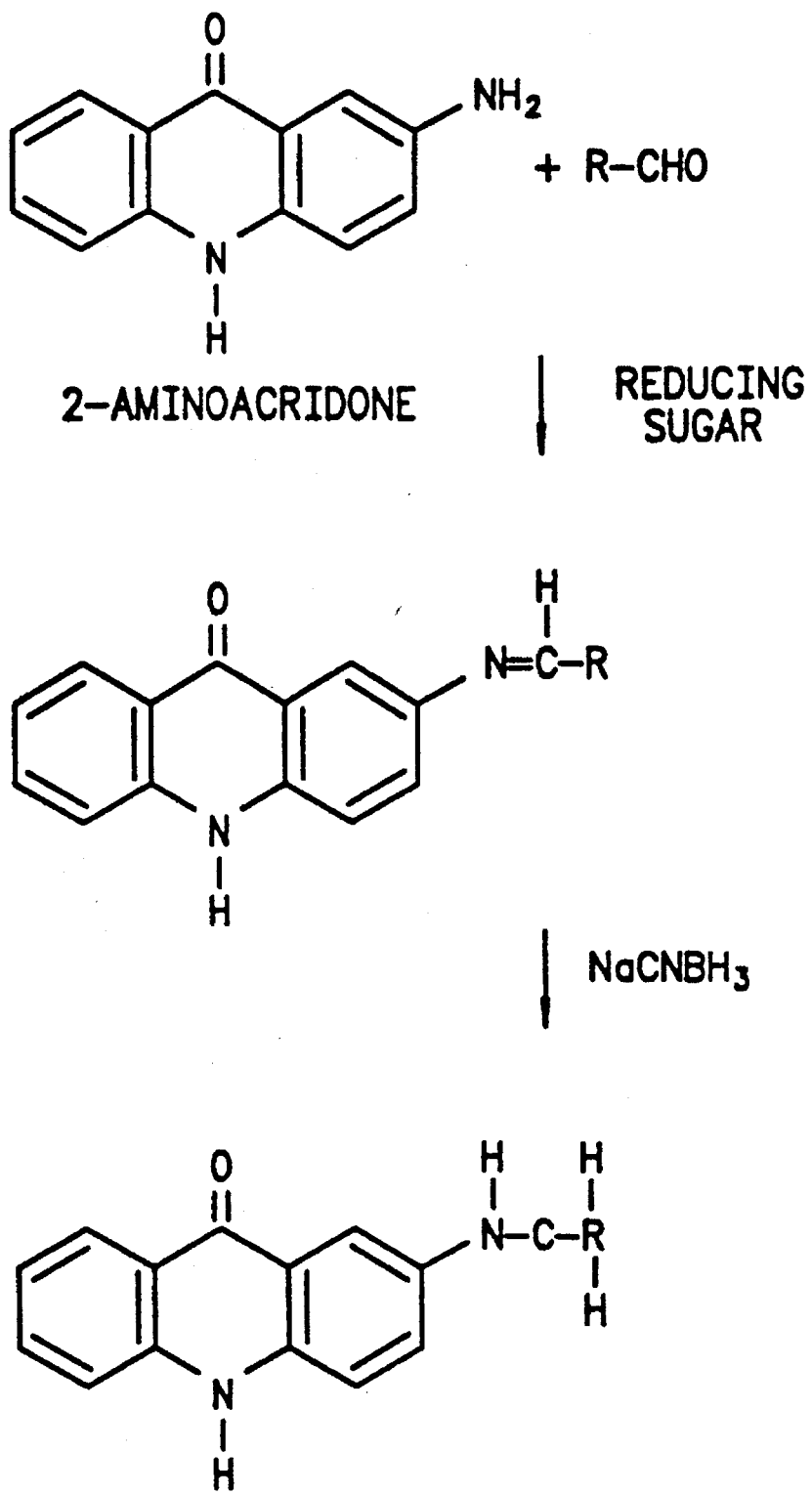
FIG. 1 illustrates the structure of 2-aminoacridone and the reaction thereof with a reducing sugar.

DESCRIPTION OF SPECIFIC EMBODIMENTS 2-aminoacridone reacts with the reducing end groups of carbohydrates, producing highly fluorescent derivatives capable of electrophoretic separation. An example of the labeling reaction is provided in FIG. 1. 2-aminoacridone itself confers no charge on labelled carbohydrates under the conditions (e.g. of alkaline pH) frequently used for electrophoretic separation. For derivatives of neutral carbohydrates, it is thus necessary to include a component, e.g. borate ions, which will confer charge onto the saccharide derivative and so enable separation. This is not necessary for negatively charged acidic saccharide derivatives (but these will nevertheless electrophorese in certain borate-containing systems), so the technique enables neutral and acidic saccharides to be easily distinguished.

Carbohydrates labeled by 2-aminoacridone may be represented according to the formula:

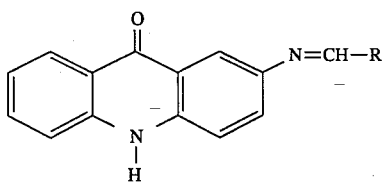

(I)

wherein R is a carbohydrate having a reducing end group.

The subject invention also provides for 2-aminoacridone labelled carbohydrates that have been reduced so as bear a charge, this permitting migration in an electric field. A reduced 2-aminoacridone labeled carbohydrate may be represented by the formula:

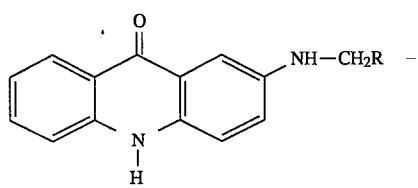

(II)

wherein R is a carbohydrate having a reducing end group.

The term "carbohydrate" includes molecules that are completely carbohydrate and glycoconjugates such as glycoproteins, glycolipids, proteoglycans, glycosphingolipids, and the like.

Among the uses of 2-aminoacridone labeled carbohydrates is the use as marker standards for the identification of unknown carbohydrates labeled by 2-aminoacridone. Similarly 2-aminoacridone labeled carbohydrates of known concentration may be used to quantitate the amount of a carbohydrate of interest in a sample for analysis.

2-aminoacridone may also be used in two-dimensional gel electrophoresis. Two-dimensional (2-D) gel electrophoresis is a well known procedure generally used to obtain very good resolution of proteins. In such techniques, a first electrophoretic separation in a first dimension is followed by a second electrophoretic separation in a second, transverse direction. Hitherto, however, it has not been possible to achieve effective 2-D gel electrophoresis of carbohydrate substances. Two-dimensional electrophoresis separation of carbohydrates labeled with a fluorophore different than 2-aminoacridone, i.e., 8-aminonapthalene-1,3,6-trisulphonic acid has been described in U.S. Pat. No. 4,975,165.

The present invention is in part based on the discovery that use of 2-aminoacridone for labelling carbohydrate substances can enable 2-D gel electrophoresis of carbohydrate substances and that 2-amino acridone labelling may be employed in conjunction with two dimensional or one dimensional electrophoresis to allow the separation and quantitation of carbohydrates within a mixture of carbohydrates.

The method of the subject invention may be applied to disease diagnosis as follows. A tissue or fluid sample taken from a patient containing a mixture of carbohydrates is labelled with 2-amimoacridone and electrophoretically separated. The amount of specific carbohydrates in the original mixture is quantitated after detection of the labelled carbohydrates by UV illumination or a charge coupled device. By comparing the quantity of specific carbohydrates, i.e., diagnostic carbohydrates, present in patient samples for analysis with the diagnostic carbohydrate level present in an individual without the disease of interest, a variety of disease conditions may be diagnosed. Another application of the present invention is the diagnosis of carriers of genetic diseases.

Another application of the present invention is to provide methods for the diagnosis of diseases that may be characterized by altered levels of diagnostic carbohydrates where the method employs the step of treating patient samples, or portions of patient samples, with carbohydrate-modifying enzymes capable of using diagnostic carbohydrates as substrates. By looking for the changes in banding patterns (as determined by fluorophore-assisted carbohydrate electrophoresis) attributable to the activity of the enzyme, the diagnosis of various diseases may either be established or confirmed.

Another application of the present invention is to provide for the early detection of diseases in infants. A diagnostic standard may be included in the electrophoretic separation.

Disease conditions capable of being diagnosed by the subject invention include carbohydrate metabolism disease, auto-immune diseases, infectious disease, exposure to toxic chemicals, and cancer. The subject invention may be used on samples obtained from humans or animals preferably, mammals.

The gel employed in the subject invention preferably comprises a relatively dense polyacrylamide gel, having a concentration in the range 15% to 60%, preferably 20% to 40%, although in some cases it may be possible or preferable to use gels of lower concentration.

The gel may be either of uniform concentration, or in the form of a gradient gel.

The gel is preferably cross linked, e.g. with N,N'-methylenebisacrylamide (bis).

One presently preferred gel comprises a 20% w/v polyacrylamide gel containing 0.67% w/v bis.

For good resolution and sensitivity, the gel may be run using a stacking buffer system (also known as moving boundary electrophoresis, multiphasic zone electrophoresis and other names), using techniques known for working with protein and DNA fragments, e.g. as described in the book "Gel Electrophoresis of Proteins: A Practical Approach", edited by B. D. Hames and D. Rickwood, published by IRL Press. However, it is not essential to use a stacking buffer system and good results can be obtained with continuous buffer systems.

Electrophoresis may also be conveniently carried out using the discontinuous electrophoretic buffer system described in Neville, Jr., D. M. (1971) J. Biol. Chem. 246, 6328–6334, which contains borate ions, but with sodium dodecyl sulphate (SDS) omitted throughout.

Two particularly suitable electrophoretic buffer systems are: a continuous Tris-borate buffer system as described in Weitzman, S. Scott, V. & Keegstra, K. (1979) Anal. Biochem. 97, 438–449; and a discontinuous Tris-HCL/Tris-glycine buffer system as described by Laemmli (naemmli, U.K. (1970) Nature (London) 227, 680–685), with sodium dodecyl sulphate (SDS) omitted throughout.

After running the gel, the labelled carbohydrate substances, when illuminated with light of suitable wavelength, e.g. ultra violet, may be visible with the naked eye in some cases, although better resolution and sensitivity may be obtained by imaging with a CCD.

CCD's are semiconductor imaging devices that permit the sensitive detection of emitted light. CCDs and their uses are described U.S. Pat. Nos. 4,874,492 and 4,852,137.

Upon suitable excitation, 2-aminoacridone fluoresces strongly with a yellow emission and a high quantum yield both before and after reaction with reducing saccharides. The emission is well suited for detection by a CCD, which has greatest sensitivity and quantum efficiency at the red end of the spectrum and lowest sensitivity and quantum efficiency at the blue end of the spectrum. Use of a CCD also has the advantage of giving readily quantitated results very quickly. Good quantitative results are easily available with a CCD due to its wide linear dynamic range. Further, a CCD can be used to view the gel while it is being run.

It is preferred to use a cooled CCD, operating in slow scan readout. One example of a suitable CCD system is the CCD 3200 Imaging System produced by Astromed Limited, Cambridge, United Kingdom. The CCD is preferably cooled to at least as low as $-25°$ C., with sensitivity being significantly increased by further cooling down as far as $-160°$ C. Typical operation temperatures are in the range $-40°$ C. to $-20°$ C.

The 2-aminoacridone labelling reagent may be attached to sites on the carbohydrate substances, after release if necessary, from an attached biomolecule. Alternatively, the biomolecule may be modified in known way to enable incorporation of the 2-aminoacridone labelling reagent.

A carbohydrate substance may be labelled with 2-aminoacridone by incubating the substance with 2-aminoacridone, possibly in the presence of a reducing agent, e.g. sodium cyanoborohydride. The sodium cyanoborohydride is preferably in solution in dimethylsulfoxide (DMSO). For good labelling, it is found useful to add the 2-aminoacridone in solution in a mixture of acetic acid and DMSO, e.g. containing 15 parts by volume of acetic acid to 85 parts by volume of DMSO.

The rate of migration of substances undergoing electrophoresis varies with the size (molecular weight) and structure of the substances. The invention may thus be used to obtain information on the size and shape of carbohydrate substances, and by comparing results with those for known standards, it may be possible partly or fully to characterize an unknown carbohydrate substance. One use of the invention is in elucidating carbohydrate structures by cleaving an unknown carbohydrate into smaller fragments, adding an additional carbohydrate moiety, esterifying the carbohydrate or epimerizing the carbohydrate by use of a carbohydrate modifying enzyme and identifying the resulting fragments.

The term "carbohydrate-modifying enzyme" as used herein refers to enzymes that can catalyze a chemical reaction wherein at least one of the reactants is a carbohydrate. It will be appreciated by the person of average skill in the art of biochemistry or organic chemistry that catalysts capable of catalyzing carbohydrate-modifying reactions that are not carbohydrate enzymes may, in certain circumstances be used in place of carbohydrate modifying enzymes. These other catalysts may include lectins, antibodies (abzymes), organic and inorganic catalysts, and a variety of proteins not traditionally considered enzymes but capable of acting similarly to enzymes, e.g., lactalbumin in lactose synthesis. The term "enzymes" as used herein refers to carbohydrate-modifying enzymes, unless indicated otherwise. Carbohydrate-modifying enzymes may alter the structure of the substrate carbohydrates in a variety of ways, including the reverse hydrolysis of linkages between saccharide units (transglycosidation by hydrolases), the formation of new linkages between saccharide units by glycosyltransferases, esterification with esterases, and epimerization with epimerases. Carbohydrate-modifying enzymes include hydrolases, lyases, acetylases, sulfatases, phosphatases, kinases, epimerases, methylases, amidases, transferases, and the like. Carbohydrate-modifying enzymes are said to have a "carbohydrate-modifying activity." The term "carbohydrate-modifying activity" refers to the reactions catalyzed by the carbohydrate-modifying enzyme of interest.

In experiments, numerous monosaccharides and oligosaccharides were derivatized at their reducing end groups with 2-aminoacridone. The resulting fluorescent compounds were separated by polyacrylamide gel electrophoresis using the two particularly suitable buffer systems mentioned above. One of these, the Tris-borate buffer, enabled all of the fluorescent saccharide derivatives tested to be electrophoresed and various positional isomers, anomers and epimers could be separated. The other system, consisting of a discontinuous Tris-HCl/Tris-glycine buffer, enable the electrophoresis of acidic, but not neutral, saccharides. The acidic and neutral saccharides could thus be distinguished unequivocally. The fluorescent labelling procedure was virtually quantitative and as little as 0.63 pmol could be detected photographically when gels were illuminated by uv light. When gels were viewed using an imaging system based on a charge-coupled-device, as little as 0.2 pmol was detected.

According to the present invention there is provided a method of separating or distinguishing reducing carbohydrate substances by 2-D gel electrophoresis, comprising fluorescently labelling reducing carbohydrate substances by reaction with 2-aminoacridone, and subjecting the labelled carbohydrate substances to electrophoretic separations in 2 dimensions.

In one preferred method of the invention when used for 2-D separation, acidic reducing carbohydrates labelled with 2-aminoacridone (2-AA) are subjected to isoelectric focusing (IEF) in polyacrylamide gel in the first dimension, followed by polyacrylamide gel electrophoresis (PAGE) in the second dimension.

In this 2-D electrophoresis technique, the acidic reducing saccharides are derivatized by a reaction at their reducing end groups charged with the fluorophore 2-AA. When charged, this fluorophore donates positive charge(s) to the derivative. The amount of positive charge depends on the pH of the solution and arises from the protonation of either the 2-AA ring nitrogen or the secondary amino group generated in the derivatization reaction, or both of these. (Knowledge of the exact pKs of these two groups is not important in understanding the principle or practice of the method.) A consequence is that the derivatives of acidic, but not neutral, saccharides will be zwitterions and suitable for analysis by IEF in a system containing ampholytes with a suitable pH range.

IEF is conveniently carried out in low concentration polyacrylamide gel rods using ampholytes with a nominal range of pH 2.5–4 in high proportion. After focusing, the gel rods are extruded from their tubes and placed directly on top of the second dimension polyacrylamide slab gel (preferably 20% w/v).

The second dimension separation is conveniently similar to the one-dimensional method for 2-AA derivatized reducing saccharides which is described previously.

The first-dimension IEF-gels, after positioning end-to-end on the second-dimension gels, are sealed in place with agarose and electrophoresed by vertical slab PAGE in a discontinuous buffer system described by Neville (Neville, Jr., D. M. (1971) J. Biol. Chem. 246, 6328–633) but with SDS omitted throughout. The system operates at alkaline pH where the 2-AA derivatives are both negatively charged and fluoresce. It should be noted that the Neville buffer system is different from either of the buffer systems previously described for the one dimensional electrophoresis separation of 2-aminoacridone labeled carbohydrates. The separation is dependent on the effective size, net charge, structure and the interaction with borate ions of the saccharide derivatives.

Using this technique, it has been found possible to analyze on a single 2-D gel a complex biological sample, namely human urine. This sample gave a pattern of fluorescent spots spread widely across the gel. The pattern of fluorescent spots obtained from human urine suggests that the parameters determining the separations in the first dimension are unrelated to those determining the second dimension separation.

The method may find application in the rapid analysis of samples of mixtures of reducing saccharides which cannot be resolved by simple one-dimensional methods.

In an alternative method of 2-D electrophoresis of the invention, the first dimension electrophoresis is carried out in an acidic gel buffer system, followed by second dimension electrophoresis in a continuous buffer system containing borate ions at alkaline pH.

In another method of the invention, the first dimension electrophoresis is carried out using a discontinuous system operating at alkaline pH, without borate ions, followed by second dimension electrophoresis generally as for the preferred method described above (i.e. with borate ions). Alternatively, borate ions may be used in the first dimension separation but not in the second dimension separation.

The subject invention also includes kits for performing the 2-aminoacridone labeling of carbohydrates. These kits for the 2-aminoacridone labeling of carbohydrates may be further used to provide for the electrophoretic separation of 2-aminoacridone labeled carbohydrates and/or the identification of carbohydrates substances labeled by 2-aminoacridone. The kits provide collections of reagents required for performing the 2-aminoacridone labeling of carbohydrates. Suitable kits enable laboratories to conveniently perform 2-aminoacridone labeling. Kits may include reagents for performing tests to identify one or more specific carbohydrate substances. Kits may include carbohydrate identification standards, 2-aminoacridone, instructions, sample containers, polyacrylamide gel reagents, and IEF reagents. More complete kits may include equipment for performing one or two dimensional electrophoresis, such as the gel apparatus CCDs, computers, software for analysis of electrophoresis band patterns, and the like. Reagents in the kits are preferably provided in premeasured amounts. The kits may also include the instructions for carrying out 2-aminoacridone labeling of carbohydrate substances and/or the electrophoretic separation of 2-aminoacridone labeled carbohydrate substances.

EXAMPLES.

The following examples are offered for the purpose of illustrating the invention and should not be interpreted as limiting the invention.

I. One-Dimensional Electrophoresis

MATERIALS AND METHODS

Materials

Saccharides (see Table 1) were obtained from either Sigma Chemical Co. (Poole, Dorset, U.K.) or Aldrich Chemical Co. (Gillingham, Dorset, U.K.). The complex oligosaccharides 42 and 43 (See Table 1) were obtained from Biocarb Chemicals (Russel Fine Chemicals, Chester, U.K.) and 2-aminoacridone was from Lambda Probes (Graz, Austria). Sodium cyanborohydride ($NaCNBH_3$) was obtained from Aldrich Chemical Co.

Derivatization of reducing saccharides with 2-Aminoacridone

For the standard derivatization 5 or 10 ul of an aqueous 1 mM or 0.5mM solution of saccharide was lyophilized in a microcentrifuge tube using a centrifugal vacuum evaporator (CVE). 5 ul of a 0.1M solution of 2-aminoacridone in glacial acetic acid/DMSO (3:17, v/v) and 5 ul of 1.0M aqueous $NaCNBH_3$ were added, the mixture was incubated at 37° C. for 15 h, lyophilized in a CVE for 4 h at approximately 40° C. and dissolved in sufficient 6M-urea solution so the 1.0 ul contained 20 pmol of saccharide. The reaction is illustrated in FIG. 1. Labelled saccharides were stored at −70° C. The concentration of 2-aminoacridone required for optimal labelling was determining by derivatizing together 10 nmol of three test saccharides, galactose-6sulphate, galactosyllactose, and maltopentaose using the standard conditions but with a range of concentrations of 2-aminoacridone. 50 pmol of each saccharide, both derivatized and free, was loaded per gel lane. The samples were electrophoresed using the Tris/borate buffer system, the gels photographed when illuminated by UV light (360 nm) and the extent of reaction determined by densitometry of the film negatives as described previously (Jackson, P. (1990) Biochem. J. 270, 705–713). In a separate experiment, glucose was analyzed in a similar way.

Electrophoresis

Samples, usually 1.0 μl or 2.0 μl, were electrophoresed in 20% w/v polyacrylamide gels containing 0.67% w/v, N,N'-methylene bisacrylamide. The final concentrations of N,N,N'N'-tetramethylenediamine and ammonium persulphate were 0.1%v/v and 0.1% w/v, respectively. A Hoefer Scientific Instruments (Newcastle Under Lyme, Staffordshire, U.K.) SE600 vertical slab gel electrophoresis apparatus was used with 8 cm (nominal) long glass plates. Pyrex glass was used when gels were viewed by the CCD system. The gel dimensions were 140 mm wide by 0.5 mm thick. the sample well were 2 mm wide. Two electrophoretic buffer systems were used: one was continuous, containing 0.1M Tris-borate buffer pH 8.3 (Weitzman, S. Scott, V. & Keegstra, K. (1979) Anal. Biochem. 97, 438–449) (the final concentration of Tris (Trizma base, Sigma) was 0.1M, the pH was adjusted with boric acid at approximately 22° C.); the other was a discontinuous Tris-HCl/Tris-glycine buffer system described by Laemmli (Laemmli, U.K. (1970) Nature (London) 227, 680–685), with SDS omitted throughout and a resolving gel 65 mm long. In both cases, the gels were cooled by surrounding analyte at +7° C. In the Tris-borate system, the samples were electrophoresed initially at 100 V for 30 min, then at 200 V for 30 min and finally at 500 V for approximately 90 min. For the Tris-HCl/Tris-glycine system, voltages used were 50 V for 30 min, 100 V for 30 min, 200 V for approximately 60 min and 500 V for approximately 60 min. The voltages were all held constant. Bromophenol blue was used as a marker and electrophoreses were stopped when it reached 10 mm from the anodic end of the gel. After the electrophoresis, the sample wells were rinsed with water, using a syringe and fine needle, to remove excess 2-aminoacridone which remained therein.

Photography and Densitometry

Gels were removed from their cassettes, and photographed after they had been positioned on a uv light box with a maximum wavelength of either 302 nm (Transilluminator TM40, U.V.P. Cambridge, U.K.) or, for the densitometric measurements, 360 nm (TF 35L New Brunswick Scientific, Hatfield, U.K.). A Wratten 8 gelatin filter (Kodak), an aperture of f4.5 and exposure time of 50 sec (unless otherwise stated) and a Polaroid-type 55 film (ISO 50) which gave both a positive and negative image, were used.

Quantification of the Fluorescent Labelling Using Glucose 2-aminoacridone was reacted, using the standard conditions, with various quantities of glucose ranging from 1.9 nmol to 52 nmol per reaction tube, each of which contained 0.5 uCi of $^{14}C$ glucose. After the reaction, 90 ul of water was added to each tube and 1.0 ul of each mixture applied to a silica-gel TLC plate (Polydram SILG: 20 cm×20 cm; MachereyNagel) and chromatographed in a solution of butan-1-ol/ethanol/water, (5:3:2, by vol). The chromatogram was autoradiographed using a Cronex 4 X-ray film (DuPont). Known quantities of unchanged $^{14}C$-glucose were chromatographed as standards.

Gel Imaging Using the Cooled CCD

Gels were imaged electronically without being removed from their electrophoresis cassettes (pyrex glass) using the Astromed (Cambridge, U.K.) 2200 Imaging System using a CCD cooled to approximately 245° K essentially as described previously (Jackson, P. (1990) Biochem. J. 270, 705–713). The gels were illuminated from a 100W tungsten-halogen lamp through a fiber-optic light guide with an exit slit 200 mm by 0.5 mm. The anodic edge of the gel was abutted to and aligned with light guide so that the illuminating light was directed in the plane of the gel. The exciting light was filtered using a 3 mm thick Schott BG3 filter (Schott Glaswerke, Mainz, Germany). The emitted light was detected through an interference filter with a transmission maximum of 530 nm (Omega Optical, Brattleboro, Vt.). The gels were viewed for either 2 seconds, or 10 seconds, or 60 seconds, and the images processed electronically to compensate for any point to point unevenness in the intensity of the illuminating light. The fluorescence of the saccharide bands in the gels was measured by determining the mean number of photons registered/min per pixel in a defined rectangular area covering each band and subtracting the gel background measured on similar adjacent blank areas in the same gel lane.

RESULTS

Derivatization of the Saccharides with 2-Aminoacridone

Figure 2:
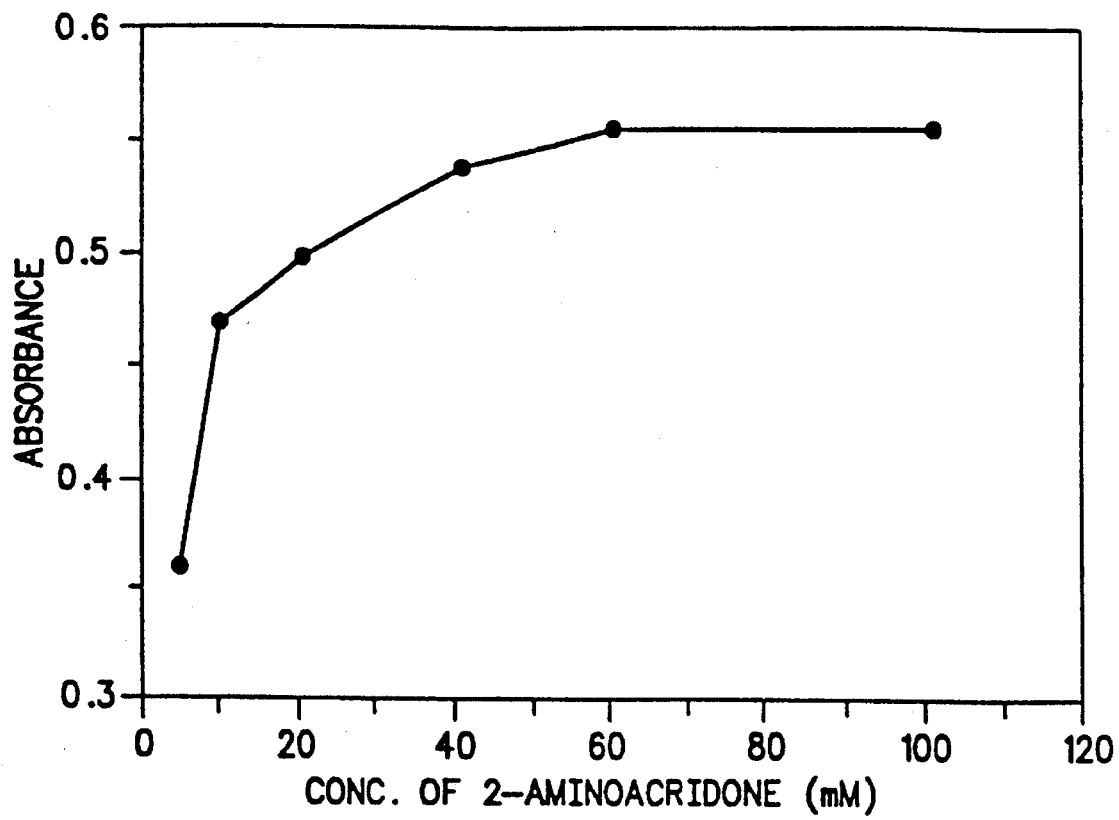
FIG. 2 is a graph of absorbance versus concentration of 2-aminoacridone, illustrating the degree of labelling of Gal-6-$SO_3$ with varying quantities of 2-aminoacridone. Each point represents the mean absorbance of four determinations. The standard errors for any value were all less than 6.1% of any mean.

The variation in the degree of derivatization of the Gal-6-SO$_3$, as the concentration of 2-aminoacridone was altered is shown graphically in FIG. 2. For the maximum derivatization, a concentration of 2-aminoacridone of at least 60 mM in the added solution was required and 100 mMwas used for the standard conditions. Glucose, galactose- 6SO$_3$ and galactosyllactose showed similar response curves although the maximum mean fluorescence of each saccharide varied by up to 12% of the mean of the maxima of all four saccharides.

The proportion of $^{14}C$-glucose which was derivatized with 2-aminoacridone in the standard conditions was determined by visual inspection of the autoradiographies of the TLC analyses of the reaction products. For all samples in the range tested, from 1.9 to 52 nmol of glucose per reaction tube, virtually all of the $^{14}C$-glucose was derivatized and appeared as a spot having a mobility significantly greater than that of the unreacted glucose.

Sensitivity of Detection and Quantitative Analysis

Serial dilutions of a standard reaction mixture containing 10 nmol of each of the three test saccharides, maltopentaose, galactosyllactose and galactose-6-sulphate, were made and samples electrophoresed in the Tris-borate buffer system. When the gels were illuminated on a UV light box (302) nm maximum emission wavelength) as little as 0.63 pmol could be detected photographically in a single band. Optimal sensitivity was obtained using an exposure time of 100 seconds. Longer exposure times caused no further increase in sensitivity as the background fluorescence masked any increased saccharide band fluorescence. The photographic system was of similar sensitivity to the human eye.

Figure 3:
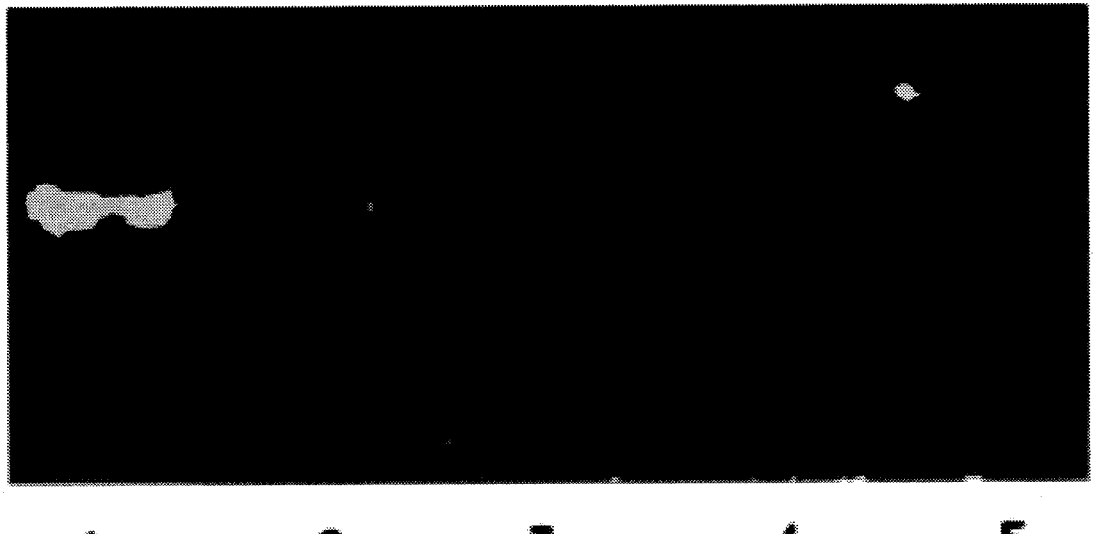
FIG. 3 is a CCD image illustrating the sensitivity of detection of Gal-6-$SO_3$ derivatized with 2-aminoacridone.

FIG. 3 illustrates serially diluted samples of Gal-6-SO$_3$ derivatives with 2-aminoacridone electrophoresed using the Tris-borate buffer system and viewed using a cooled CCD imaging system. The numbers in the figure include pairs of lanes with similar loadings, and the lanes are as follows: lanes 1, 0.8 pmol; lanes 2, 0.4 pmol; lanes 3, 0.2 pmol; lanes 4, 0.1 pmol; lanes 5, sample buffer alone. As little as 0.2 pmol was detected.

Figure 4:
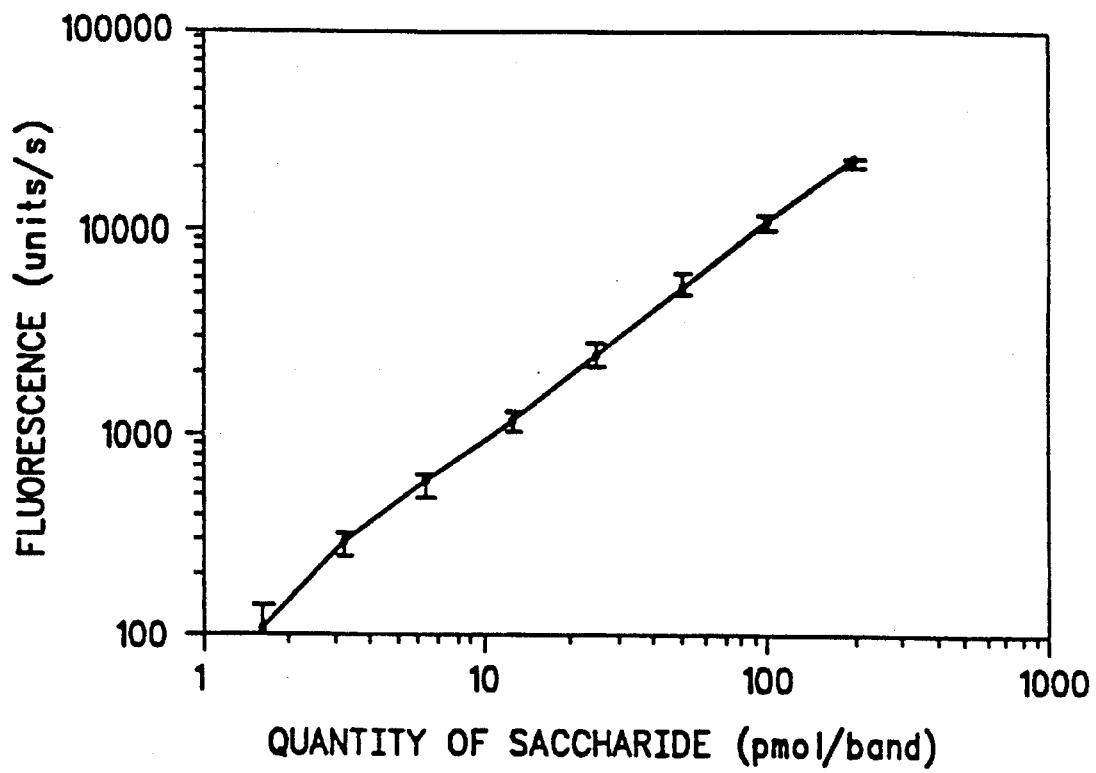
FIG. 4 is a graph of fluorescence versus quantity of saccharide, illustrating the variation of the CCD response with the quantity of 2-aminoacridone labelled Gal-6-SO$_3$ per gel band.

The response of the CCD imaging system to varying quantities of Gal-6-SO$_3$ labelled with 2-aminoacridone using the standard conditions is shown in FIG. 4. In FIG. 4, each point represents the mean and standard error for each of four determinations. The fluorescence units are: - the mean net photons registered per 10 second per CCD pixel per saccharide band. The double logarithmic plot was used to encompass conveniently all of the data over the range 3 pmol to 200 pmol per gel band.

TABLE 1

Saccharides analysed

| | Abbreviated formula | Trivial name |
|---|---|---|
| 1 | 2-deoxy-D-Gal | 2-deoxygalactose |
| 2 | 6-deoxy-D-Gal | L-fucose |
| 3 | 2-deoxy-D-Glc | 2-deoxyglucose |
| 4 | 6-deoxy-D-Glc | 6-deoxyglucose |
| 5 | D-Gal | galactose |
| 6 | α-D-Glc | glucose |
| 7 | D-Man | mannose |
| 8 | 3-O-Methyl-α-D-Glc | 3-O-methylglucose |
| 9 | D-GalNac | N-acetylgalactosamine |
| 10 | α-D-GlcNac | N-acetylglucosamine |
| 11 | α-D-Gal-(1-4)-D-Gal | galactosylgalactose |
| 12 | β-D-Gal-(1-6)-D-Gal | galactobiose |
| 13 | β-D-Gal-(1-4)-α-D-Glc | -lactose |
| 14 | α-D-Gal-(1-6)-D-Glc | mellibiose |
| 15 | β-D-Gal-(1-4)-D-Man | galactosylmannose |
| 16 | α-D-Glc-(1-4)-D-Glc | maltose |
| 17 | β-D-Glc-(1-4)-D-Glc | cellobiose |
| 18 | α-D-Glc-(1-3)-D-Glc | nigerose |
| 19 | β-D-Glc-(1-3)-D-Glc | laminaribiose |
| 20 | α-D-Glc-(1-6)-D-Glc | isomaltose |
| 21 | β-D-Glc-(1-6)-D-Glc | gentiobiose |
| 22 | α-D-Man-(1-3)-D-Man | mannobiose |
| 23 | α-D-Glc-(1-4)-α-D-Glc-(1-4)-α-D-Glc | maltotriose |
| 24 | β-D-Glc-(1-4)-β-D-Glc-(1-4)-β-D-Glc | cellotriose |
| 25 | α-D-Glc-(1-6)-α-D-Glc-(1-4)-α-D-Glc | panose |
| 26 | α-D-Glc-(1-6)-α-D-Glc-(1-6)-α-D-Glc | isomaltotriose |
| 27 | (α-D-Glc-(1-4)$_3$α-D-Glc | maltotetraose |
| 28 | α-D-Glc-(1-6)-(α-D-Glc-(1-4)-)$_2$α-D-Glc | |
| 29 | (α-D-Glc-(1-4)-)$_4$α-D-Glc | maltopentaose |
| 30 | (α-D-Glc-(1-4)-)$_5$=-D-Glc | maltohexaose |
| 31 | (α-D-Glc-(1-4)-)$_6$α-D-Glc | maltoheptaose |
| 32 | β-D-Gal-(1-4)-D-GlcNac | N-acetylactosamine |
| 33 | β-d-Gal-(1-4)-D-GlcNac | diacetylchitobiose |
| 34 | β-D-GlcNac-(1-4)-β-D-GlcNac-(1-4)-D-GlcNac | triacetylchitobiose |
| 35 | D-Gal-6-SO3 | galactose-6-sulphate |
| 36 | D-Glc-6-SO3 | glucose-6-sulphate |
| 37 | D-GlcNac6SO3 | N-acetylglucosamine-6-sulphate |
| 38 | D-GlcA | glucuronic acid |
| 39 | Neu5Gl | N-glycolylneuraminic acid |
| 40 | Neu5Ac | N-acetylneuraminic acid |
| 41 | Neu5Ac-(2-3)-β-D-Gal-(1-4)-D-Glc | N-acetylneuraminlactose |
| 42 | Neu5Acα2-3Galβ1-3(Fucα1-4)GlcNacβ1-3Galβ1-4Glc | monosialyl, monofucosyllacto-N-tetraose |
| 43 | Neu5Acα2-6Galβ1-4Glc Nacβ1-6(Fucα1-2Galβ1-3GlcNacβ1-3)Galβ1-4Glc | monofucosyl, monosialyllocto-N-hexaose |

Electrophoretic Separation in the Tris-Borate Buffer System

Figure 5A:
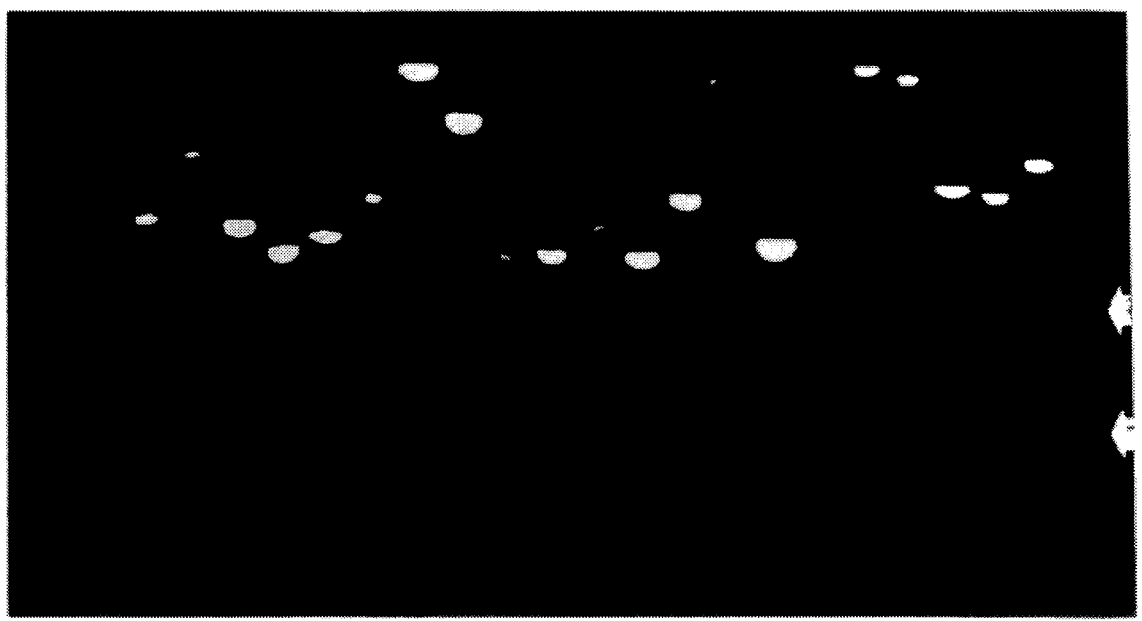
FIGS. 5a and 5b are CCD images of two fluorescent electrophoretograms showing a range of saccharides labelled with 2-aminoacridone and separated by PAGE using the Tris-borate buffer system.
Figure 5B:
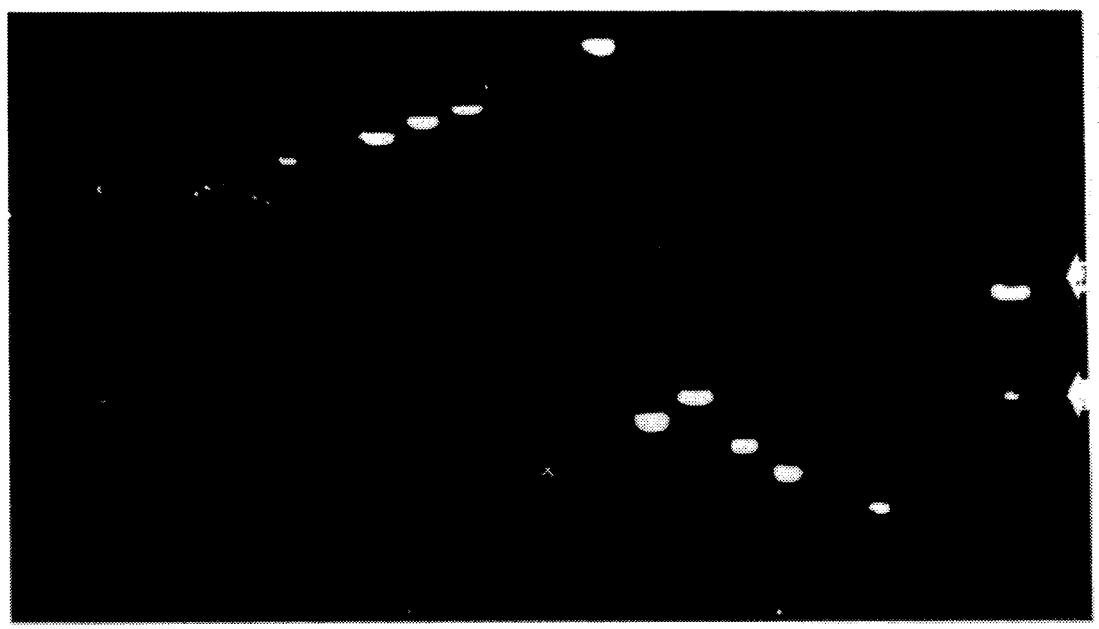

In FIGS. 5a and 5b are shown CCD images of fluorescent electrophoretograms were made of gels using the Tris-borate buffer system, of a variety of mono- and oligosaccharides labelled with 2-aminoacridone. The gels were viewed for 30 seconds for each image section. The samples run of the gels corresponds to the number of each of the saccharides shown in Table 1. The lanes labelled "W" are controls and contained no saccharide in the labelling reaction. The arrows show the positions of artifactual bands. 20 pmol of each of the saccharides analyzed was visible as a bright yellowish band. Faint bluish bands were also present in all the samples, including the water blank at the positions indicated in FIGS. 5a and 5b and FIG. 7. These bands were easily distinguishable by eye from the yellow saccharide bands when gels were viewed on a UV light box and moved faster than all of the neutral saccharides tested. More of these bands are visible in FIG. 7 than in FIG. 5 since a larger proportion of the reaction mixture was analyzed in the gel shown in FIG. 7. A bright yellow band occurred at the cathodic end of each gel lane owing to the unreacted 2-aminoacridone which was uncharged at the pH of the electrophoresis. Most of the unreacted 2-aminoacridone was removed by rinsing the sample wells prior to both CCD imaging and before disassembling the gel cassette for photography. In the latter case, any fluorophore which had diffused onto the gel was removed by cutting of the top 1–2 mm.

Figure 7:
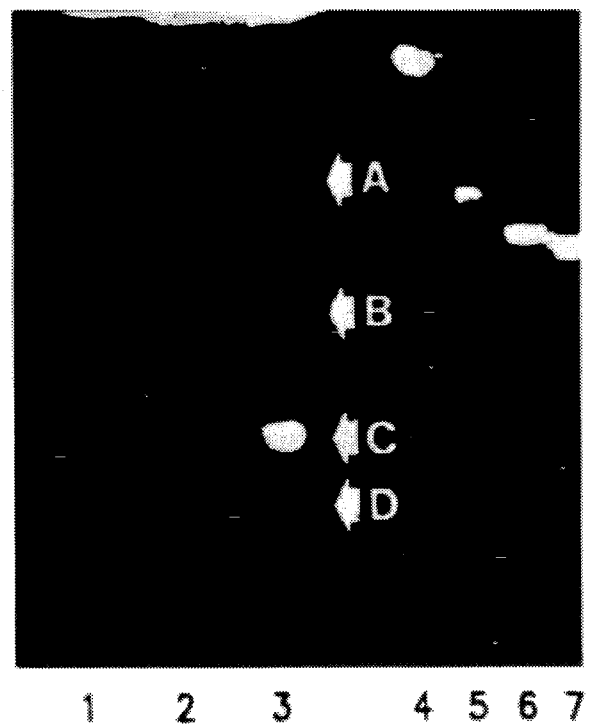
FIG. 7 is a CCD image of a fluorescent electrophoretogram showing the positions of artifactual bands and various neutral saccharide derivatives.

FIG. 7 is a CCD image of a fluorescent electrophoretogram showing the positions of artifactual bands and various neutral saccharide derivatives. The gel was viewed for 60 seconds. Each of lanes 1, 2 and 3 contain a proportion of a standard reaction mixture which contains no saccharide. The reaction mixture was dissolved in 100 μl of 6M-urea, and the lanes are as follows: lane 1, 0.5 μl; lane 2, 1.0 μl; lane 3, 2.0 μl. The arrows labelled A, B, C and D show the positions of the major artifactual bands which appeared bluish when viewed on a UV light box. The remaining lanes show four neutral reducing saccharides: lane 4, 3-O-methlyglucose; lane 5, mannose; lane 6, glucose; lane 7, galactose. 10 nmol of each saccharide derivative was dissolved in 500 ul of 6M-urea and 20 pmol (1 μl) loaded per lane.

The mobilities of the labelled saccharides were dependent partly on the size of each saccharide molecule but were also strongly influenced by various molecular structures. Thus the effect of the size of a saccharide can be seen from examining the mobilities of glucose and all its straight chain alpha 1–4 linked oligomers from maltose to maltoheptaose (FIG. 5a, lane 16, and FIG. 5b, lanes 23, 27, 29, 30 and 31) which showed a decreasing mobility with increasing degree of polymerization. However, in some cases large differences in mobility could be seen between various positional isomers. For instance, corresponding 2 and 6 deoxy derivatives of galactose and glucose were well separated and the six dimers of glucose were well separated into 3 pairs of anomers, nigerose and laminaribiose (1–3 linked), maltose and cellobiose (1–4 linked), and isomaltose and gentiobiose (1–6 linked). In addition, the corresponding anomers in each pair had small mobility differences and this was also the case for maltotriose and cellotriose. In all cases where the corresponding pairs of anomers were tested, the beta-linked molecules had slightly higher mobilities than those were alpha-linked.

Other small structural differences led to relatively large mobility differences, for instance, the epimers galactose, glucose and mannose were separated from each other, and N-acetylgalactosamine and N-acetylglucosamine were separated widely. It was noticed that linkage of glucose through the 3-hydroxyl led to a marked reduction in mobility compared with related molecules as shown by 3-O-methylglucose, nigerose and laminaribose. The N-acetylated compounds N-acetyl lactosamine, diacetylchitobiose and triacetylchitobiose were also significantly retarded relative to other saccharides of similar size.

The electrophoretic mobilities of the acidic saccharides in the Tris-borate buffer system was also affected by small structural differences; for instance, galactose-6-sulphate and glucose-6-sulphate were separated. In general they had higher mobilities than the neutral saccharides. The three mono-saccharides which contained a carboxyl group, glucuronic acid, N-glycolylneuraminic acid and N-acetylneuraminic acid each showed three separate bands. The reasons for this phenomenon is at present unknown. It was not seen with N-acetylneuraminlactose or the sialylated complex oligosaccharides 42 and 43 (see Table 1).

Electrophoresis in the Tris-HCl/Tris-Glycine Buffer System

Figure 6:
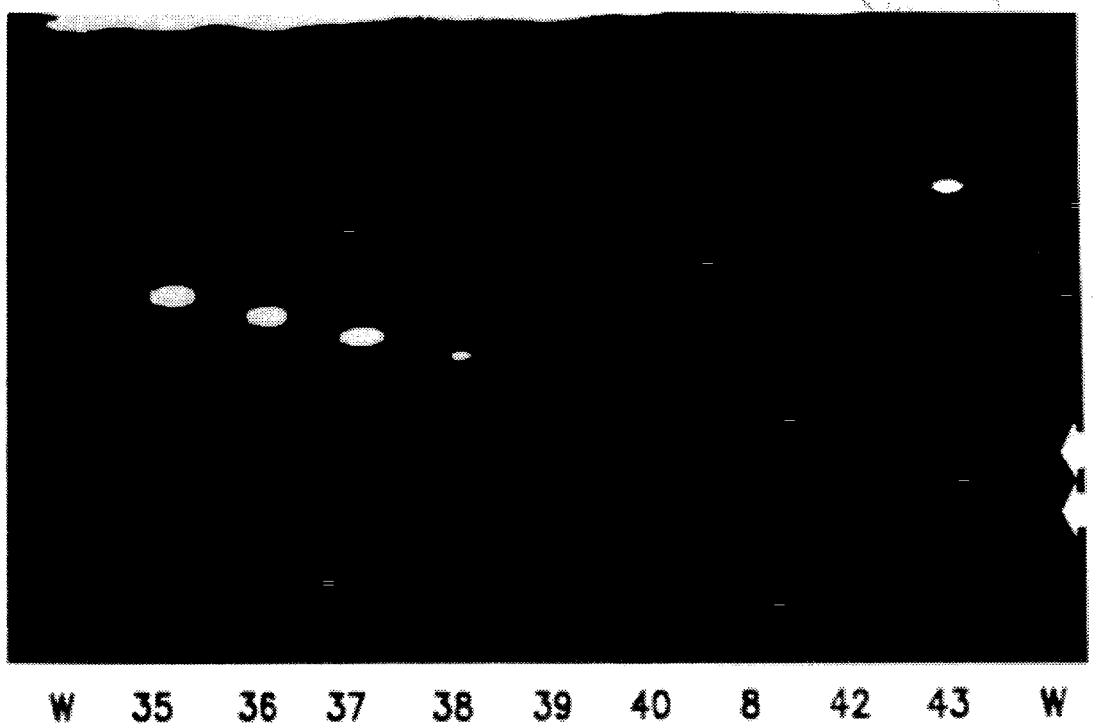
FIG. 6 is a CCD image of a fluorescent electrophoretogram showing only acidic saccharides labelled with 2-aminoacridone and separated by PAGE using the Tris-HCl/Tris-glycine buffer system.

None of the neutral saccharides were detected when electrophoresed in the Tris-HCl/Tris-glycine buffer system. However, the 2-aminoacridone derivatives of all the acidic saccharides were electrophoresed into the gel as is shown in FIG. 6, which is a CCD image of a fluorescent electrophoretogram showing only acidic saccharides labelled with 2-aminoacridone and separated by PAGE using the Tris-HCL/Tris-glycine buffer system. Approximately 20 pmol of each saccharide derivative is shown. The gel was viewed for 30 seconds for each image section. Each gel lane number corresponds to the number of each saccharide shown in Table 1. The lanes labelled "W" are controls and contained no saccharide in the labelling reaction. The arrows show the positions of artifactual bands.

Glucuronic acid, N-glycolylneuraminic acid, and N-acetylneuraminic acid, but not N-acetylneuraminlactose appeared as three bands which were fainter than the other saccharides. Non-saccharide bands, which had a bluish fluorescence when viewed on a uv light box, were present in all the samples including $H_2O$. These bands migrated ahead of the saccharide band (see FIG. 6).

DISCUSSION

PAGE, i.e., polyacrylamide gel electrophoresis, has been used previously for the separation of oligosaccharides which are charged naturally (Rice, K. G., Rotrink, M. K. & Linhardt, R. J. (1987) Biochem J. 224, 515–522; Turnbull, J. E. & Gallagher J. T. (1988), Biochem J. 251, 597–608; Turnbull, J. E. & Gallagher, J. T. (1990) 265, 715–724; Al-Hakim, A. & Linhardt, R. J. (1990) Electrophoresis II, 23–28) and also for the separation of uncharged oligosaccharides as borate ion complexes (Weitzman, S. Scott, V. & Keegstra, K. (1979) Anal. Biochem. 97, 438–449; Foster, A. B. (1957) Advan. Carbohyd. Chem. 12, 81–115 Fuller, K. W. & Northcote, D. H. (1956) Biochem J. 64, 657–6619). Numerous methods for the covalent labelling of reducing saccharides with fluorophores have been described (Wang, W. T., LeDonne, Jr., N. C., Ackerman, B. & Sweeley, C. C. (1984) Anal. Biochem. 141, 366–381; Hase, S., Ikenaka, T. & Matsushima, Y. (1979) J. Blochem. (Tokyo) 85, 989–994; Prakash, C. & Vijay, I. A. (1983) Anal. Biochem. 128, 41–46; Ingham, K. & brew, S. A. (1981) Anal. Blochem. 128, 41–46; Carson, S. D. (1977) Anal. Biochem. 78, 428–435; Honda, S., Iwase, S., Makino, A. & Fujiwara, S. (1989) Anal. Biochem. 176, 72–77; Jackson, P. & Williams, G. R. (1988) International Patent Specification W088/10422) although PAGE has been used in only two recent reports (Jackson, P. (1990) Biochem. J. 270, 705–713; Jackson, p. & Willams, G. R. (1991) Electrophoresis 12, 94–96; Jackson, P. & Williams, G. R. (1988) International Patent Specification W088/10422) for the analysis of such derivatives.

In the present work, a novel a method of PAGE has been described in which all of the highly fluorescent 2-aminoacridone saccharide derivatives tested could be electrophoresed in a buffer system containing borate ions. The 2-aminoacridone itself conferred no charge on the labelled saccharides at the pH of the electrophoretic system gel. Thus the derivatives of neutral saccharides did not move in 3the electrophoretic buffer which contained no borate ions, in contrast to the negatively charged acidic saccharide derivatives. As a result, the method enabled neutral and acidic saccharides to be distinguished easily.

The method was simple and relatively rapid to perform and used inexpensive, commercially available reagents. The reaction conditions were based on those used previously for the quantitative derivatization of reducing saccharides by an aromatic primary amine, 8-aminonaphthalene- 1-3-6-trisulphonic acid (ANTS) (Jackson, P. (1990) Biochem. J. 27.0., 705–713) and the conditions chosen gave quantitative derivatization for the 2-aminoacridone.

The method described shows high sensitivity using either photography or electronic imaging with the cooled CCD. The latter system is approximately three times more sensitive and there is considerable potential for increasing its sensitivity by increasing the power of the light source, by matching the filters more accurately to the excitation and emission spectra of the fluorophore, by using a CCD camera cooled to a lower temperature, and by using a wider aperture lens. However, in practice, the sensitivity of detection may be limited by the proportion of the reaction mixture which can be loaded into the sample wells. When using the system described, this volume is 10 µl. Since the minimum volume of the 6M-urea sample solution required to dissolve the reaction mixture material is 50 µl, only one fifth of the available saccharide derivative can be loaded. However, it is possible to increase the proportion loaded by almost fivefold by reducing the volume of the reactants to 1 µl.

A second limit on the sensitivity of detection may arise from the artifactual bands which are labelled in FIGS. 5, 6 and 7. These bands are of little importance when detecting the neutral saccharides, which all have mobilities less than bands B, C and D (see FIG. 7) and the fourth band (band A, FIG. 7) is faint and coincident with only a few of the neutral saccharides. One of the acidic saccharide derivatives (Glc-6-$SO_3$) has a mobility identical with that of the major artifactual band (band C in FIG. 7). However, all of the acidic saccharide derivatives are detectable in the alternative non-borate buffer system where the major artifactual bands are a lesser problem having mobilities greater than any of the acidic saccharide derivatives (see FIG. 6).

The 2-aminoacridone based PAGE analysis of reducing saccharides described here is in principle similar to that in which ANTS has been used and reported previously (Jackson, P. (1990) Biochem. J. 270, 705–713). The ANTS enabled all the reducing saccharides tested to be visualized in a single gel with high resolution without using borate ions in the electrophoresis buffer. The fluorescent saccharide bands are considerably sharper in the ANTS system than those obtained using 2-aminoacridone and the electrophoretic mobilities of the ANTS derivatives were influenced strongly by the size of each molecule. Thus, all of the alpha 1–4 linked straight chain polymers of glucose from maltose to (alpha-D-Glc-(1–4))$_{25}$alpha-D-Glc were separated in a single gel. However, neutral and acidic saccharide derivatives were all negatively charged by the ANTS molecule. Therefore, they were not readily distinguishable electrophoretically as two groups of molecules, unlike those labelled with 2-aminoacridone. The electrophoretic mobilities of derivatives of the latter reagent are much less influenced by the saccharide sizes but are much more strongly affected by the saccharides structures.

Numerous separations could be obtained with 2-aminoacridone but not with ANTS. For instance, galactose and mannose derivatives were separated and much greater difference in the mobilities of the various positional isomeric dimers and trimer of glucose were demonstrated. The unequivocal differentiation of neutral and acidic sugars may be a particularly useful property of 2-aminoacridone.

It seems likely that the analytical properties of the 2-aminoacridone-based method described here will complement that of the ANTS method. The simplicity of using the cooled CCD imaging system to view the gels in vitro, while at the same time enabling high sensitivity and rapid quantitation, should be useful for the enzymological analysis of naturally occurring complex carbohydrates.

II. Two-Dimensional Electrophoresis

First Dimension: Isoelectric focusing

Derivatization of reducing saccharides with 2-aminoacridone was performed essentially as in Example I.

Isoelectric focusing was carried out in a small uniform bore glass capillary tubes (approx. 0.8 mm i.d.) (Vitres, 44.7 μl, marked volume, Camlab, Cambridge U.K.). The IEF gel was 65 mm long and the solution was made as follows:

| | |
|---|---|
| acrylamide (30% w/v) N,N$^1$-methylenebisacrylamide (0.8% w/v) | 0.4 ml |
| ampholyte LKB 2.5–4 | 0.075 ml |
| ampholyte Pharmacia 3–10 | 0.025 ml |
| Nonidet P40/H$_2$O soln. (1:9, v/v) | 0.05 ml |
| ammonium persulphate soln. (10% w/v) | 0.02 ml |
| TEMED | 0.002 ml |
| H$_2$O, degassed to | 2.0 ml |

The anolyte was made by diluting 0,375 ml of concentrated H$_2$SO$_4$ in 250 ml of degassed H$_2$O. The catholyte was 20 mMNaOH made by diluting 0.5 ml stock 10M NaOH in 250 ml degassed H$_2$O, The IEF gel was overlayed with approx. 30 ul of ampholyte solution (Pharmacia pH range 3–10 (5% v/v)). The samples were dissolved in 6M-urea and layered under the ampholyte solution in the gel tube. Usually 0.5 to 2 ul was loaded. It was ensured that no air bubbles occurred in the system. Bromophenol blue in solution in 6M-urea was also loaded to act as a marker.

Saccharide derivatives were focused at 100 V for 30 min. and then at 1000 V for 60 min. In the later stages of the focusing the bromophenol blue, which turned yellow, appeared as an immobile band.

Gels were removed from their tubes by gentle water pressure and placed across the top of a second vertical slab gel. Two gels were placed end to end on each second dimensional gel.

Second Dimension

The second dimension was a uniform concentration (20% w/v) polyacrylamide gel with the dimensions 70mm (H)× 140 mm (W) x 0.75 mm (T). The buffer system was based on that of Neville (Neville, Jr., D. M. (1971) J. Biol. Chem. 245, 6328–6334). The gel solution contained 20% (w/v) acrylamide, 0.67% bis, 0.1% w/v ammonium persulphate, 0.01% v/v TEMED, ).042M Tris HCl buffer pH 9.18. The anolyte was 0.42M tris HCl buffer pH 9.18 and the catholyte was 0,041M Trisbase, 0.04M boric acid, pH 8.64.

The IEF-gels were sealed in place with approx. 3 mm of 1.0% w/v agarose solution buffered with the stacking gel buffer for the electrophoretic system used (Neville, Jr., D. M. (1971) J. Biol. Chem. 246, 6328–6334), that is 0.054M Tris base, 0,027M H$_2$SO$_4$, pH 6.1. The samples were electrophoresed at 100 V for 30 min., 200 V for 30 min. and 500 V for 60 min. The voltages were held constant and the gel cooled by surrounding anolyte at approximately +7° C. The electrophoresis was stopped when the bromophenol blue from the first dimension gel reached approximately 5 mm from the anodic end of the gel.

The gel was rinsed and either viewed using the Astromed CCD 2200 imaging system in vitro or removed from its cassette and photographed as described in example 1.

Figure 8:
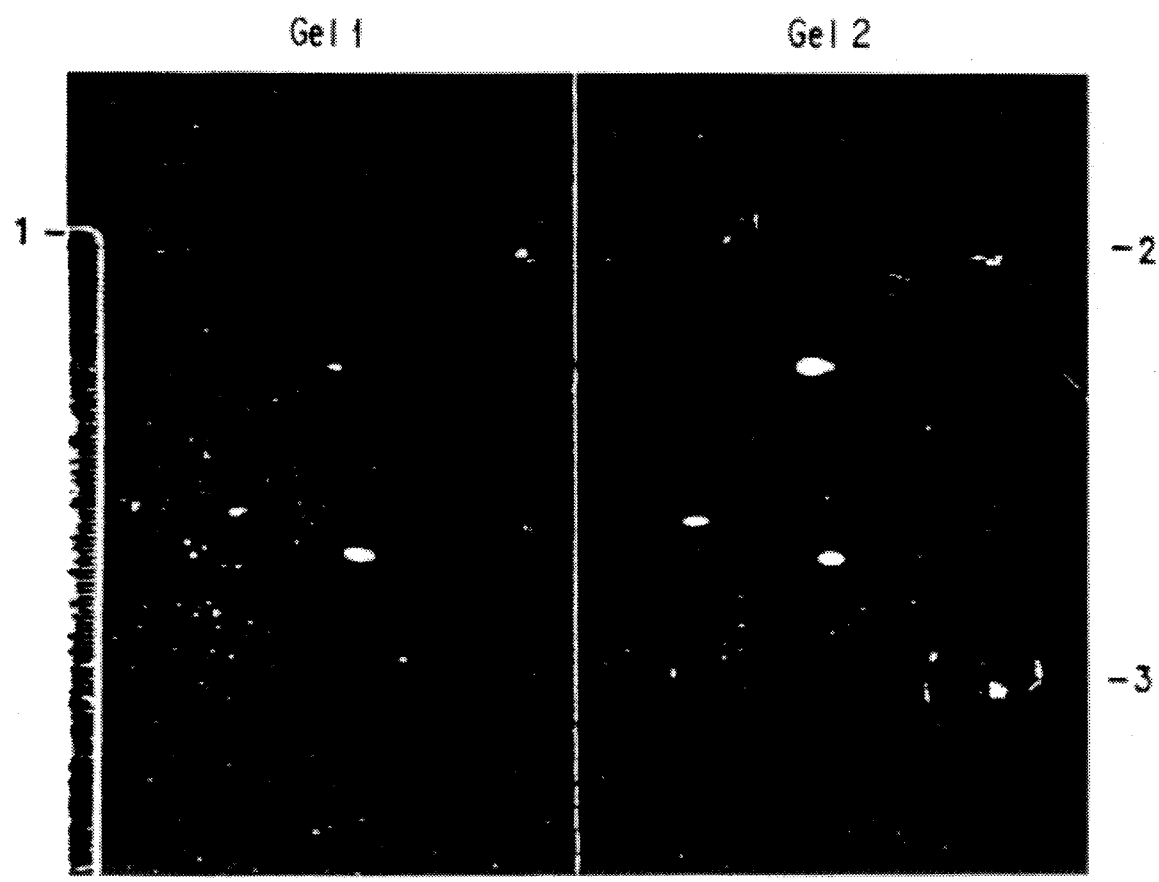
FIGS. 8 and 9 are CCD images of 2-D gels obtained using IEF for the first dimension.
Figure 9:
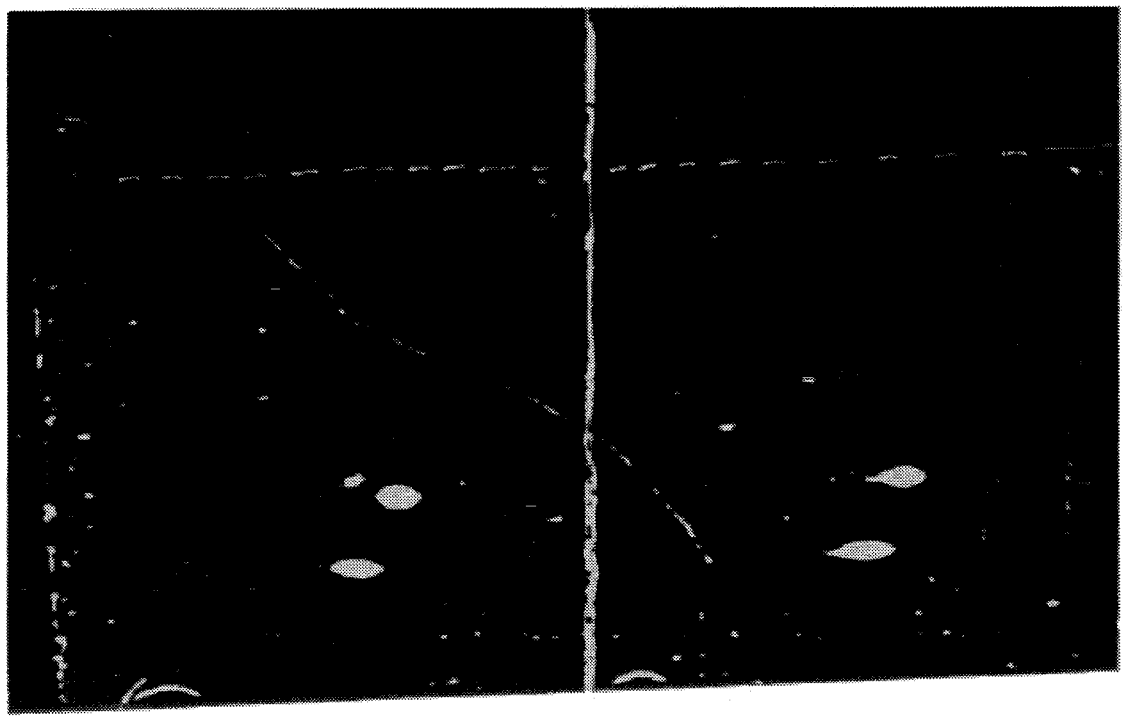

Photographs of CCD images of typical two-dimensional fluorescent electrophoretograms are shown in FIGS. 8 and 9.

FIG. 8 shows two IEF gels indicated at 1 and 2, each having the acid end at the left hand side as shown in the Figure, placed side to side (i.e., end to end) on the second dimension gel which was run in a downwards direction as shown in the Figure. The bottom of the second dimension gel is shown at 3.

Two two-dimensional gels were run as described above, with complex oligosaccharide 56/51 (Biocarb catalogue No. 56/51) and neuraminidase on gel 1 and complex oligosaccharide 56/51 on gel. 2.

The central spots towards the upper end of the second dimension gels are of oligosaccharide 56/51, with the spot in gel 1 being diminished compared with the spot on gel 2. The uncharged reaction product of the digestion of oligosaccharide 56/51 by neuraminidase is not seen on the gel. Other spots are of unknown identity or are artifacts.

FIG. 9 is similar to FIG. 8, with the left hand gel showing results for urine and neuraminidase and the right hand gel showing results for urine. The diagonal line running across the two gels is a photographic artifact.

Further experiments were carried out using electrophoresis rather than IEF for the first dimension separation. The following Examples were carried out using equipment and methods generally as described in Example 2 apart from the differences detailed below.

Example 3

Samples were electrophoresed in an acidic gel buffer system which operates at approximately pH 2.71 for the first dimension. All the neutral saccharide derivatives and some of the acidic saccharide derivatives will be positively charged at this pH. The second dimension was on a continuous buffer system containing borate ions at pH 8.3. All the saccharide derivatives will be negatively charged in this system.

Figure 10:
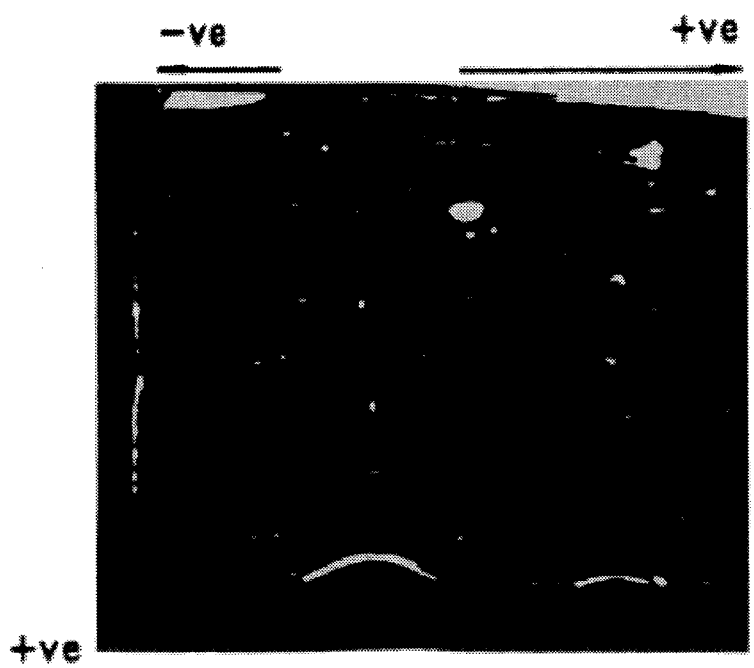
FIGS. 10 and 11 are CCD images of 2-D gels obtained using electrophoresis for the first dimension.

FIG. 10 is a photograph of a CCD image of the results obtained for a urine separation by this method.

Example 4

Samples were electrophoreses in a buffer system based on that of naemmli (Laemmli, U.K. (1970) Nature (London) 227, 680–685), but with SDS omitted from the first dimension. This is a discontinuous system operating at alkaline pH and contains no borate ions. The second dimension buffer system was based on that of Neville (Neville, Jr., D. M. (1971) J. Biol. Chem. 246, 6328–6334) but the SDS omitted throughout. This system contains borate ions. The gel pattern depends on the differential interaction of saccharide derivatives with borate ions.

Figure 11A:
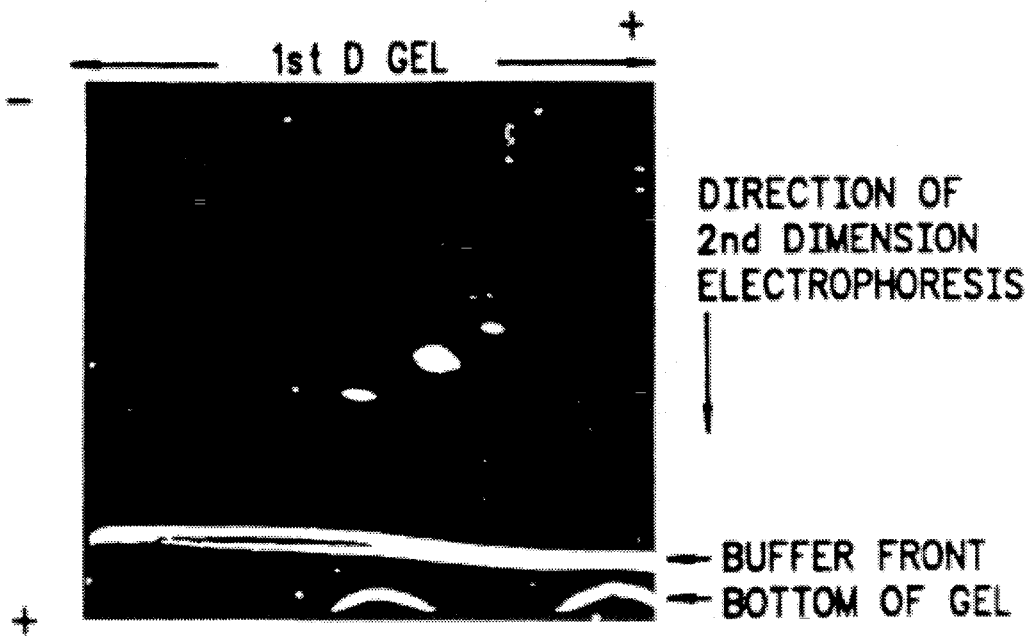
Figure 11B:
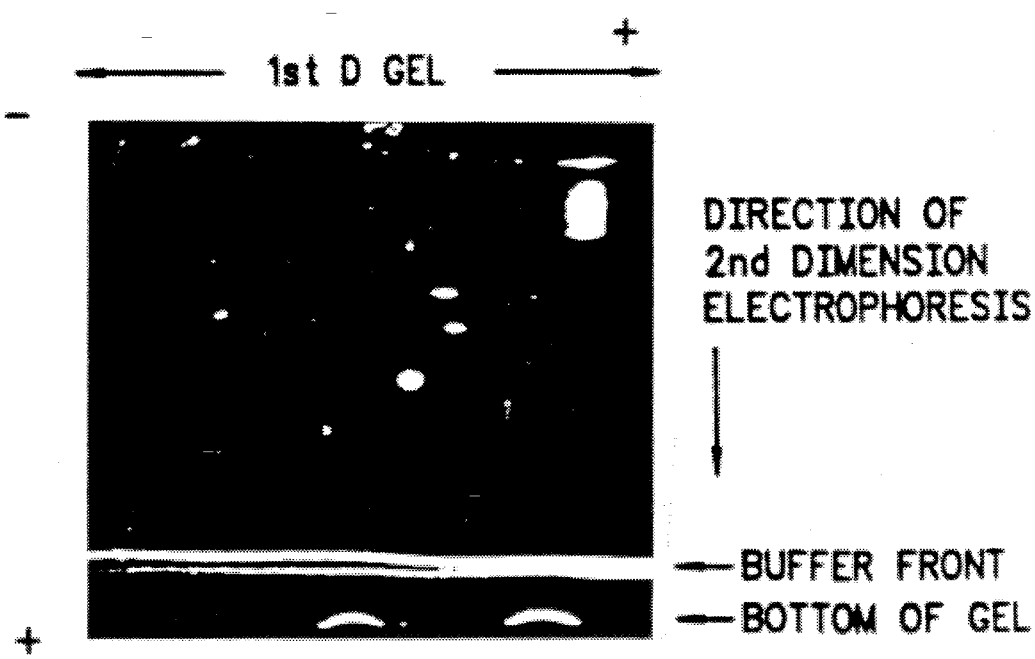

FIGS. 11a and 11b are photographs of CCD images of results obtained for a complex mixture of 40 saccharides (FIG. 11a) and also for urine (FIG. 11b).

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

EQUIVALENTS

The foregoing written specification is considered to be sufficient to enable one skilled in the art to practice the invention. Indeed, various modifications of the above-described modes for carrying out the invention which are obvious to those skilled in the field of analytical chemistry or related fields area intended to be within the scope of the following claims.

I claim:

1. A method of labelling a carbohydrate, said method comprising the step, adding 2-aminoacridone to said carbohydrate.

2. A method according to claim 1 wherein said carbohydrates are labelled in the prescence of a reducing agent.

3. A method of separating a mixture of carbohydrates, said method comprising the steps, labelling said carbohydrates by the method of claim 1, separating said carbohydrates from one another by electrophoresis.

4. A method according to claim 3, said method further comprising the step, visualizing said separated carbohydrates by illumination.

5. A method according to claim 3, said method further comprising the step, visualizing said separated carbohydrates by a charge-coupled device.

6. A method of analyzing the structure of a carbohydrate, said method comprising the steps, labelling said carbohydrate according to the method of claim 1, treating said carbohydrate with a carbohydrate modifying enzyme whereby, at least one new carbohydrate is formed, separating said carbohydrates by electrophoresis.

7. A method according to claim 6, wherein said carbohydrate modifying enzyme is selected from the group consisting of glycosidases, glycosyl transferases, carbohydrate esterases, epimerases, hydrolases, lyases, acetylases, sulfatases, phosphatases, kinases, methylases, and amidases.

8. A method according to claim 6, said method further comprising the step, visualizing said carbohydrate by illumination.

9. A method according to claim 6, said method further comprising the step, visualizing said carbohydrate by a charge-coupled device.

10. A method according to claim 3, wherein said electrophoresis is two-dimensional.

11. A method according to claim 10, wherein one dimension of said two-dimensional electrophoresis is separated by isoelectric focusing.

12. A method according to claim 10, wherein at least one dimension of said electrophoresis is in a continuous buffer system containing borate ions at alkaline pH.

13. A method according to claim 6, wherein said electrophoresis is two-dimensional.

14. A method according to claim 13, wherein at least one dimension of said electrophoresis is in a continuous buffer system contains borate ions at alkaline pH.

15. A method according to claim 13, wherein one dimension of said two-dimensional electrophoresis is separated by isoelectric focusing.

16. A kit for labelling, separating, or structurally analyzing carbohydrates said kit comprising, 2-aminoacridone and carbohydrate modifying enzymes.

17. A kit according to claim 16, wherein said carbohydrate modifying enzymes are selected from the group consisting of glycosidases, glycosyl transferases, carbohydrate esterases, epimerases, hydrolases, lyases, acetylases, sulfatases, phosphatases, kinases, methylases, and amidases.

18. A carbohydrate labeled by the method of claim 1.

19. A labeled carbohydrate having the formula

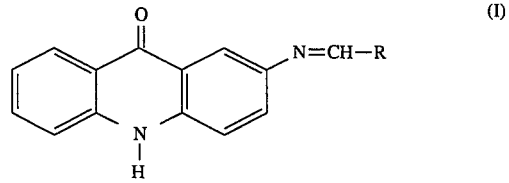

wherein R is a carbohydrate.

20. A labeled carbohydrate having the formula

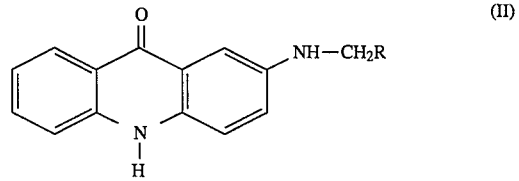

wherein R is a carbohydrate.

* * * * *